United States Patent [19]

Buchele

[11] Patent Number: 4,480,481

[45] Date of Patent: Nov. 6, 1984

[54] MEANS AND METHOD FOR SOIL TESTING

[75] Inventor: Wesley F. Buchele, Ames, Iowa

[73] Assignee: Iowa State University Research Foundation, Inc., Ames, Iowa

[21] Appl. No.: 468,462

[22] Filed: Feb. 22, 1983

[51] Int. Cl.³ .............................................. G01N 3/00
[52] U.S. Cl. ........................................ 73/784; 73/843; 73/845
[58] Field of Search ................. 73/784, 843, 845, 848, 73/84

[56] References Cited

U.S. PATENT DOCUMENTS

| | | | |
|---|---|---|---|
| 3,116,633 | 1/1964 | Cohron | 73/784 |
| 3,364,734 | 1/1968 | Wilson | 73/784 |
| 3,465,576 | 9/1969 | Spanski | 73/784 |
| 3,797,301 | 3/1974 | Hawes | 73/784 |

FOREIGN PATENT DOCUMENTS 127059 2/1959 U.S.S.R. ................................ 73/843

*Primary Examiner*—Anthony V. Ciarlante
*Attorney, Agent, or Firm*—Zarley, McKee, Thomte, Voorhees & Sease

[57] ABSTRACT

An inexpensive device which is easily operated to accurately measure the Coulomb parameters of the soil. The Coulomb parameters are used in Coulomb's equation to calculate the shearing stresses along a failure surface of the soil. The device includes an instrument to test soil shear strength to which several weights have been added. To obtain the Coulomb parameters, the instrument is placed on the soil to be tested and weights are incrementally added to it. The instrument is rotated at each weight increment and the shearing stresses are read from its calibrated dial. The stresses are plotted on a graph from which the Coulomb parameters are determined. The shearing stress of the soil with any known force applied to it can then be determined.

16 Claims, 4 Drawing Figures

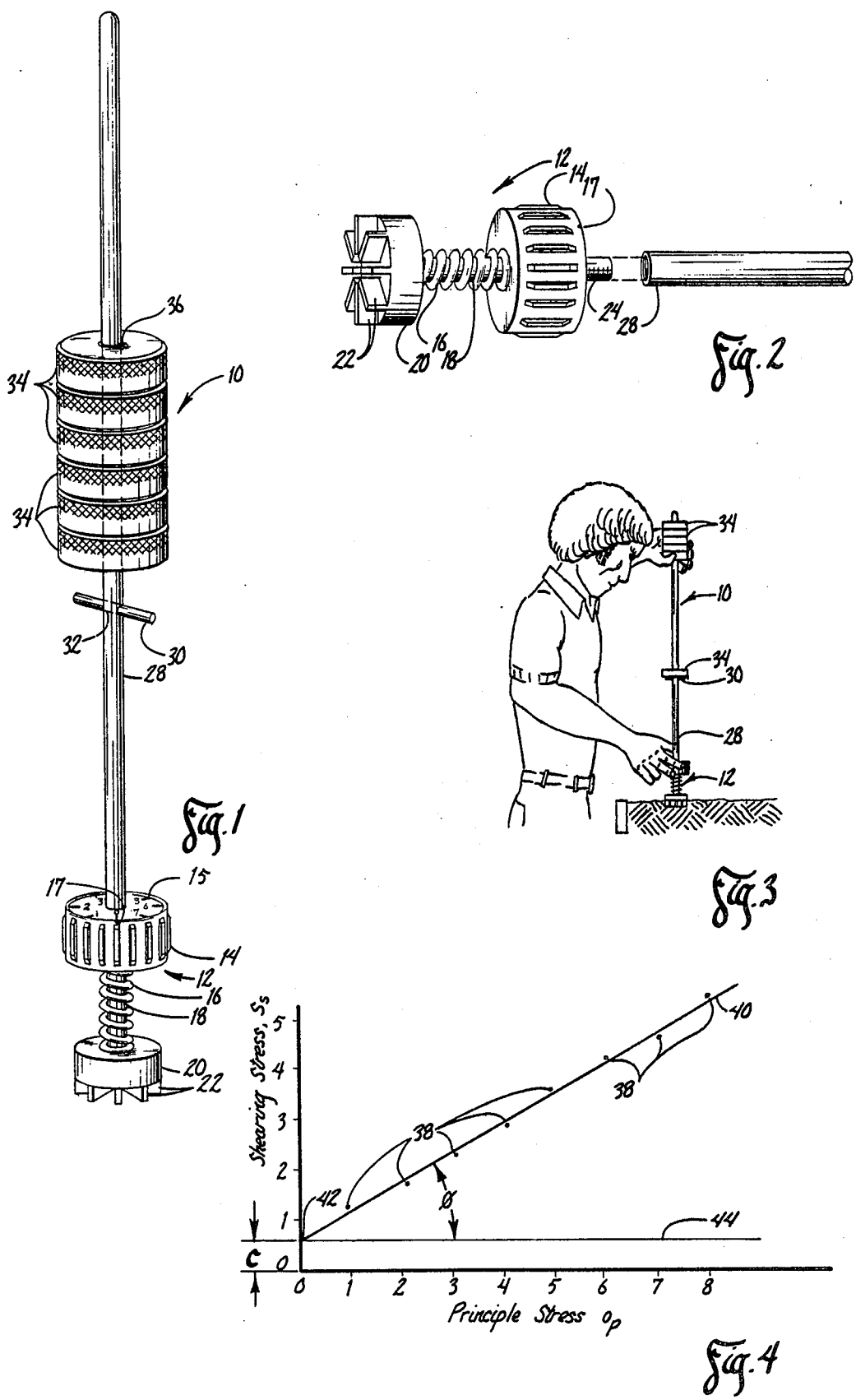

MEANS AND METHOD FOR SOIL TESTING

BACKGROUND OF THE INVENTION

The determination of Coulomb parameters (cohesion and angle of internal shearing resistance), which are needed in the Coulomb equation for the calculation of shearing stress of soil, is essential for the application of classical soil mechanics theory to construction and stability problems. Normal procedures require taking two or three undisturbed core samples of soil, carrying them to a laboratory and determining shear strength at different values of confining pressure in order to define the Coulomb relationship from which the shearing stress may be calculated. It may take two or three days to conduct these laboratory tests and to make the results known at the construction site. Also, these tests are relatively expensive. It is therefore desirable that the shearing stress tests be made at the natural site of the soil so that the results may be quickly calculated and put to use and so that the cost per test is reduced.

Most site testing methods have had the disadvantage that cohesion and angle of internal shearing resistance were not capable of being separately measured. For example, in the vane shear test, a bladed vane is pushed into the sediment and a torque is applied to cause circumferential shearing. However, the vane shear test principally measures cohesion. Attempts to measure internal friction angle have not been generally successful.

Some instruments, such as the Torvane shear strength instrument, merely provide an index reading which can be compared with other readings to determine which soil is weaker. The Torvane instrument's reading also cannot be compared to the cohesion of the soil or the angle of internal shearing resistance. Furthermore, no specific units or dimensions can be assigned nor can the strength of the soil be determined. Cone penetrometers give an indication of the strength of the soil but do not give usable information concerning the behavior thereof. Thus, conventional devices for soil testing at the site of the soil have not been able to determine shearing stresses in the soil.

It is therefore a primary objective of the present invention to provide an inexpensive means and a quick and easy method for accurately measuring the Coulomb parameters of soil at the original site of the soil.

It is a further objective of the present invention to provide a device that is economical to manufacture and durable in use.

These and other objectives will become apparent in the description of the present invention.

SUMMARY OF THE INVENTION

The soil testing device of the present invention is comprised of a cylindrical shaft attached to the longitudinal axis of a conventional soil shear strength instrument such as a Torvane instrument manufactured by Soiltest, Inc., 2205 Lee Street, Evanston, Ill. 60202. A pin extending through the shaft supports weights as they are mounted upon the shaft. The device is calibrated to indicate soil shearing stress as the weights are incrementally added to the pin.

In using the device, the operator sets the lower plate of the soil strength instrument on the soil to be tested while keeping the longitudinal axis of the device in a vertical position. For the first reading, the weights are placed onto the shaft but supported by one hand. The other hand is used to continuously rotate the torque knob of the soil strength instrument to assure that the reading is read during plastic failure. The shearing stress is read during continuous rotation and recorded. The weights are added one at a time with the torque knob being rotated each time and the shearing stress being recorded after each weight is added. After the test has been run, the shearing stress is plotted on a graph and the Coulomb parameters of the soil are determined by drawing a straight line on a graph such that the sum of the perpendicular distances from the shearing stress points to the line is minimized. The soil cohesion value "C" is equal to the point where the line intersects the Y axis at zero principle stress and the angle of shear resistance is equal to the angle between the line and a horizontal line. After these parameters for the soil are determined, the known principle and shearing stress of a structure that will be placed on the soil, such as a dam, is calculated and compared with the ability of the soil to support such a structure.

BRIEF DESCRIPTION OF THE DRAWINGS

FIG. 1 is a perspective view of the device.

FIG. 2 is a perspective view of the soil strength instrument.

FIG. 3 is a view showing an operator using the device.

FIG. 4 is a graph showing the plotted shearing stress points and the line used to determine the Coulomb parameters.

DETAILED DESCRIPTION OF THE DRAWINGS

In FIG. 1, numeral 10 generally designates the soil testing device. Numeral 12 generally designates the Torvane soil strength instrument.

The Torvane soil strength instrument has a torque knob 14, a calibrated dial 15, a torsion spring 16, reference mark 17 at zero torque value on knob 14, a shaft 18 coinciding with the longitudinal axis of the instrument, and a lower soil engaging plate 20 with vanes 22. The torque knob 14 is connected to the torsion spring 16 which is in turn connected to soil engaging plate 20. The torque required to rotate the knob is proportional to the angle of rotation. The calibrated dial 15 is fixed to shaft 18 so that when torque knob 14 is rotated, mark 17 will move with respect to dial 15. The calibrations correspond to the shearing stress in soil when a known load is applied to the soil. At the upper end of the Torvane instrument 12 is a post 24 which is the upper end of the shaft 18, and which is threaded to receive shaft 28 of the device 10. Shaft 28 has a pin 30 passing through hole 32 such that pin 30 can support a plurality of weights 34. Weights 34 are cylindrical in shape and each weight has a hole 36 having a diameter sufficiently large so that the weights may be mounted on shaft 28.

The shearing stress instrument must be calibrated before it can be used for measuring the shearing stress of the soil. The calibrated dial 15 is calibrated to read shearing stress in pounds per square inch as hereafter described.

The torque required to rotate torque knob 14 is equal to the torque required to rotate plate 20 about a common axis. Therefore, the force required to rotate the knob applied at the radius of the knob can be determined by the following equations:

$$T = \frac{2\pi(r_2^3 - r_1^3)S_s}{3}$$

Where:
T = torque, lb-in
$r_2$ = outside radius of plate 20 = 0.500 inch
$r_1$ = inside radius of plate 20 = 0.200 inch
$S_s$ = shearing stress = 1 psi
And:
T = FR
Where:
F = mass of the calibrating weight
R = radius of torque knob = 0.8 in $$F = \frac{2\pi(r_2^3 - r_1^3)S_s}{3 \cdot R}$$

$$= \frac{2\pi(0.5^3 - 0.2^3) \cdot (1)}{3 \cdot 0.8}$$

$$= 0.3063 \text{ lb}$$

Once the calibrating force is known, the calibrations on dial 15 of the device 10 can be made. An easily readable reference mark 17 at zero torque reading is made on the torque knob 14. The mark 17 may be a scratch on knob 14 or may be made in any other manner that makes the mark stand out. While the device is held horizontal with shaft 28 held tight in a vice, an index is marked on dial 15 corresponding to the position of mark 17 when no force is applied to knob 14. This index is labeled zero. A calibration weight with a mass equal to the calibrating force (not the same as weight 34) is then attached to the torque knob 14 in some manner, such as by the string secured to and wrapped around the torque knob, so that the torque knob is rotated by the force of the weight hanging from the radius of the knob. An index is marked on the dial 15 corresponding to the position of mark 17 and labeled "1". Adding one additional weight each time, this process is repeated for a total of six equal weights with an index corresponding to the position of mark 17 being marked for each succeeding weight.

The device of the present invention is used to measure the Coulomb parameters of the soil, from which in turn the shearing stresses of the soil at any other load can be calculated by using Coulomb's equation when the known load of a structure such as a dam is placed on the soil. Coulomb's equation is:

$$S_s = C + \sigma_p \tan \phi$$

Where:
C = cohesion of the soil
$S_s$ = shearing stress
$\sigma_p$ = principle stress normal to the principle axis of the device
$\phi$ = angle of internal shearing resistance of soil to be tested The present invention has modified the Torvane instrument so that known principle stresses can be placed on the soil. By placing a plurality of known principle stresses on the soil, the Coulomb parameters of the soil can be determined. When the Coulomb parameters of the soil are known, the shearing stress of the soil can be calculated when a single large known principle stress, such as the mass of a dam, is applied to the soil.

The principle stresses applied to the soil have been designed to be measured in integer numbers in units of pounds per square inch (psi) for application in Coulomb's equation. This design process involves calculating the mass of the device 10 and of each of the succeeding weights 34 to be applied to the soil so that the principle stress is 1 psi when only the device itself is positioned on the soil and will be 1 additional psi for each weight 34 placed on the device. The appropriate equation is:

$$\sigma_p = W/A$$

Then:
$$W = A\sigma_p$$

Where:
W = mass of device 10 and each of the other weights 34 (unknown)
$\sigma_p$ = principle stress 1 psi
A = area of plate 20 = 0.7854 square inches
W = $A\sigma_p$ = 0.7854·1 = 0.7854 pounds Calculation of the thickness (h) of each weight is by the following equations:

$$h = \frac{W}{\pi(r_2 - r_1)D}$$

h = thickness of weight 34
$r_2$ = outer radius of weight 34 = 1 inch
$r_1$ = inner radius of weight 34 = 0.203 inch
D = density of steel = 0.2847 lb/in³

$$h = \frac{0.7854}{\pi((1)^2 - (0.203)^2) \cdot 0.2847} = 0.9159 \text{ inch}$$

FIG. 3 shows how the device is used. Plate 20 is placed on the soil to be tested with the vanes 22 placed on the soil. The device 10 must be kept vertical at all times during use. Weights 34 are placed on the shaft 28 but not lowered onto the pin 30. The weights 34 are held by the hand and this hand may be rested against the forehead so as to provide a steady journaled bearing for shaft 28. The other hand continuously rotates the torque knob 14. The shear stress is read from calibrated dial 15 during continuous rotation at the peak shear stress, that is, the stress when the soil under plate 20 continuously shears. (The plate moves with respect to the soil.) The value of the reading is recorded so that it can later be plotted on a graph in which the X axis represents principle stress and the Y axis represents shearing stress. Thus, the X coordinate for the first shear stress reading is "1".

Using the free hand, the lower most weight 34 is gently lowered onto pin 30 such that the pin supports the weight. One hand then supports the remaining weights as it rests against the forehead as the other hand rotates the torque knob 14. The shear stress is read and recorded with the corresponding X coordinate on the graph being "2".

The above procedure is repeated until all of the weights 34 have been lowered onto the pin 30 and the corresponding shear stresses recorded. After the shearing stresses have been plotted on the graph, a straight line 40, as in FIG. 4, is then drawn on the graph such that the sum of the perpendicular distances from the shear stress points 38 to line 40 is a minimum. Line 40 is then extrapolated back to the Y axis of the graph. The cohesion value of the soil "C" is equal to the point 42 where line 40 intersects the Y axis, at which time the principle stress is equal to zero. The angle of shear resistance $\phi$ is equal to the acute angle between line 40 and a horizontal line 44.

The unknown Coulomb parameters for the soil have thus been determined from known shearing stresses using the device of the present invention. These Coulomb parameter values can then be used in Coulomb's equation to determine the unknown shearing stress of soil when a known large load, such as the mass of a building is applied to the soil.

It is understood that the values used in the above equations are for but one particular preferred embodiment and variations in the values relating to varying dimensions of a soil testing device may be used without detracting from the invention.

The present invention is thus a simple, inexpensive, easy to use, and accurate means and rapid method for accurately measuring the soil principle and shearing stress in the field or in the laboratory for later use in Coulomb's equation. The time required for reading and its analysis is less than five minutes for each set of readings. Therefore, at least all of the above stated objectives are accomplished by this invention.

What is claimed is:

1. A soil testing device used to determine the Coulomb parameters of soil, said device comprising:
   a first shaft with opposite upper and lower ends,
   a torsion spring mounted on said first shaft,
   a soil engaging plate secured to said lower end of said first shaft and having soil engaging vanes extending downward therefrom,
   a torque knob journaled about said upper end of said first shaft,
   a dial secured to said upper end of said first shaft adjacent to said torque knob and having calibrations thereon,
   a second shaft secured to said upper end of said first shaft, the longitudinal axis of said first shaft aligning with that of said second shaft,
   a plurality of weights adapted slidably receive said second shaft, and
   a means on said second shaft for supportive engagement of said weights.

2. A device according to claim 1 wherein said weights have equal mass and each of said weights is cylindrical in shape and has a hole through the longitudinal axis of said weight, said hole having a diameter sufficiently large to slidably receive said shaft.

3. A device according to claim 1 wherein said torsion spring has a first end secured to said lower end of said first shaft and an upper end secured to said torque knob.

4. A device according to claim 1 wherein the mass of said device without said weights equals the mass of each of said weights, said mass being such that the principle stress normal to the longitudinal axis of said first and second shafts is one pound per square inch for each of said masses applied to the soil, said masses being calculated by the equation $W = A\sigma_p$ wherein W equals the mass of said device without said weights and of each of said weights, A equals the area of said soil engaging plate, and $\sigma_p$ equals one pound per square inch of principle stress normal to the longitudinal axis of said first and second shafts.

5. A device according to claim 1 wherein said soil engaging plate is cylindrical in cross section with an outer edge and a central bore, said vanes extending from the outer edge to said central bore.

6. A device according to claim 5 wherein said calibrations correspond to shearing stress of soil with known force being applied to said soil.

7. A device according to claim 6 wherein said calibrations are derived by determining the force necessary to create one pound per square inch of shearing stress when said force is applied to said torque knob, said force being calculated by the equation $F = T/R$ wherein F equals said force in units of pounds, R equals the radius of said torque knob, and T equals the torque in units of pound inches applied to said torque knob with $$T = 2\pi(r_2^3 - r_1^3)S_s/3$$

wherein $r_2$ equals the outside radius of said soil engaging plate, $r_1$ equals the inside radius of said soil engaging plate, and $S_s$ equals the shearing stress in units of pounds per square inch resulting from said force being applied to said torque knob.

8. A device according to claim 1 wherein said means for supportive engagement of said weights is a pin extending through said second shaft.

9. A device according to claim 1 wherein said torque knob has a reference mark adjacent said dial.

10. A method of determining the Coulomb parameters of soil using an elongated shearometer device comprising a first shaft with opposite upper and lower ends, a torsion spring mounted on said first shaft, a soil engaging plate secured to said lower end of said first shaft and having soil penetrating vanes extending downwardly therefrom, a torque knob journaled about said upper end of said first shaft and attached to said torsion spring, a calibrated dial with markings corresponding to shearing stress of soil when known forces are applied to said soil secured to said upper end of said first shaft adjacent to said torque knob, a reference mark on said torque knob adjacent said dial, a second shaft secured to said upper end of said first shaft with the longitudinal axis of said first shafts aligning with that of said second shaft, a plurality of cylindrical weights adapted to slidably receive said second shaft, a support means on said second shaft for supportive engagement of said weights, said method being:
   placing said soil engaging plate on the soil to be tested such that said vanes penetrate the soil,
   maintaining the longitudinal axis of said device in a vertical orientation,
   periodically releasing an additional one of said weights onto said support means for support thereby whereby a constant, known principle stress is applied to the soil,
   rotating said torque knob of said shear strength instrument during continuous shearing condition of the soil after each additional weight is released,
   reading said shear stress from said calibrated dial during plastic failure of the soil during each rotation of said torque knob,
   plotting said shear stresses on a graph, and
   determining Coulomb's parameters from said graph.

11. A method according to claim 10 wherein said graph has an X axis corresponding to the principle stress applied to said device and a Y axis corresponding to the shear stress of said soil.

12. A method according to claim 10 wherein the initial reading and recording of said shear stress is made with none of said weights being released for support by said support means.

13. A method according to claim 10 wherein after each of said readings and recording of said shear stress one additional weight is applied to said device.

14. A method according to claim 10 wherein said Coulomb parameters are determined by drawing a straight line on said graph such that the sum of the perpendicular distances from the shear stress points to said line is a minimum and extrapolating said line to said Y axis of said graph, whereupon the point where said line crosses said Y axis is the cohesion value of the soil and the acute angle between said line and a horizontal line equals the angle of shearing resistance.

15. A method of determining the Coulomb parameters of soil using a shearometer device comprising a first shaft with opposite upper and lower ends, a torsion spring mounted on said first shaft, a soil engaging plate secured to said lower end of said first shaft and having soil penetrating vanes extending downwardly therefrom, a torque knob journaled about said upper end of said first shaft and attached to said torsion spring, a calibrated dial with markings corresponding to shearing stress of soil when known forces are applied to said soil secured to said upper end of said first shaft adjacent to said torque knob, a reference mark on said torque knob adjacent said dial, a second shaft secured to said upper end of said first shaft with the longitudinal axis of said first shafts aligning with that of said second shaft, a plurality of cylindrical weights adapted to slidably receive said second shaft, a support means on said second shaft for supportive engagement of said weights, said method being:

setting said soil engaging plate on the soil to be tested such that said vanes penetrate the soil, maintaining the longitudinal axis of said device in a vertical orientation, placing said weights on said device and supporting said weights with one first hand, rotating said torque knob with the other second hand during continuous shearing condition of the soil, recording said value on a graph with said second hand, releasing one of said weights by said first hand with the aid of said second hand such that said weight is supported by said support means on said second shaft whereby a constant known principle stress is applied to the soil, rotating said torque knob with said second hand while supporting said remaining weights with said first hand until the soil begins to shear, reading said shear, plotting said value on a graph with said second hand, and repeating this sequence until all of said weights have been released, and determining Coulomb parameters from said graph.

16. A method according to claim 15 wherein said Coulomb parameters are determined by drawing a straight line on said graph so as to minimize the sum of the perpendicular distances from the shear stress points to said line, and by extrapolating said line to the Y axis of said graph, whereupon, the soil cohesion value is equal to the point where said line intersects said Y axis, and the angle of shear resistance is equal to the angle between said line and a horizontal line which is parallel to said X axis.

* * * * *